US011337989B2

(12) United States Patent
Guthrie et al.

(10) Patent No.: US 11,337,989 B2
(45) Date of Patent: *May 24, 2022

(54) COMPOSITIONS AND METHODS FOR INHIBITING INFLAMMATION AND DISEASES USING AN ALGINIC ACID-BASED ANTIMICROBIAL COMPOUND

(71) Applicant: Evofem, Inc., San Diego, CA (US)

(72) Inventors: Wendell Guthrie, San Diego, CA (US); Gary S. Hahn, San Diego, CA (US)

(73) Assignee: Evofem, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/106,755

(22) PCT Filed: Dec. 19, 2014

(86) PCT No.: PCT/US2014/071664
§ 371 (c)(1),
(2) Date: Jun. 20, 2016

(87) PCT Pub. No.: WO2015/095793
PCT Pub. Date: Jun. 25, 2015

(65) Prior Publication Data
US 2016/0354394 A1     Dec. 8, 2016

Related U.S. Application Data

(60) Provisional application No. 61/918,445, filed on Dec. 19, 2013.

(51) Int. Cl.
*A61K 31/734* (2006.01)
*A61K 31/19* (2006.01)
*A61K 9/00* (2006.01)
*A61K 9/06* (2006.01)
*A61K 47/12* (2006.01)
*A61K 31/675* (2006.01)
*A61F 6/04* (2006.01)
*A61F 6/06* (2006.01)
*A61M 35/00* (2006.01)

(52) U.S. Cl.
CPC .............. *A61K 31/675* (2013.01); *A61F 6/04* (2013.01); *A61F 6/065* (2013.01); *A61K 9/0014* (2013.01); *A61K 9/06* (2013.01); *A61K 31/19* (2013.01); *A61K 31/734* (2013.01); *A61K 47/12* (2013.01); *A61M 35/003* (2013.01)

(58) Field of Classification Search
None
See application file for complete search history.

(56) References Cited

U.S. PATENT DOCUMENTS

| 4,999,342 A | 3/1991 | Ahmad et al. |
| 5,617,877 A | 4/1997 | Moench et al. |
| 5,667,492 A | 9/1997 | Bologna et al. |
| 6,468,526 B2 | 10/2002 | Chrisope |
| 6,664,296 B1 | 12/2003 | Meignant |
| 6,706,276 B2 | 3/2004 | Garg et al. |
| 8,425,894 B2 | 4/2013 | Batcheller et al. |
| 8,518,378 B2 | 8/2013 | Tamarkin et al. |
| 8,871,244 B2 | 10/2014 | Andersch |
| 9,060,933 B2 | 6/2015 | Dahl |
| 9,198,858 B2 | 12/2015 | Nordsiek et al. |
| 9,566,232 B2 | 2/2017 | Guthrie |
| 10,568,855 B2 | 2/2020 | Guthrie |
| 2002/0177624 A1 | 11/2002 | Hanna et al. |
| 2004/0009223 A1 | 1/2004 | Garg et al. |
| 2004/0242459 A1* | 12/2004 | Forrest .................. A61K 45/06 514/630 |
| 2005/0272700 A1 | 12/2005 | Buyuktimkin et al. |
| 2008/0153776 A1 | 6/2008 | Xia et al. |
| 2009/0142313 A1 | 6/2009 | Talling et al. |
| 2010/0069323 A1* | 3/2010 | Seto ..................... A61K 9/0014 514/54 |
| 2011/0020265 A1 | 1/2011 | Bafcheller |
| 2011/0104262 A1 | 5/2011 | Lulla et al. |
| 2011/0132376 A1 | 6/2011 | Dahl |
| 2011/0159091 A1 | 6/2011 | Stone et al. |
| 2013/0150810 A1 | 6/2013 | Maguire et al. |
| 2015/0080467 A1 | 3/2015 | Andersch |

(Continued)

FOREIGN PATENT DOCUMENTS

| AU | 2015201042 A1 | 9/2015 |
| CN | 1431895 A | 7/2003 |

(Continued)

OTHER PUBLICATIONS

Iwata Dumitriu et al. ed. Polysaccharides in Medicinal Applications Marcel Dekker, Inc.:New York 1996, p. 603, 622.*
Lide et al. Handbook of Data on Common Organic Compounds CRC Press: Boca Raton 1995 p. 505.*
Potassium Bitartarate MSDS 2005.*
Auras et al. Poly(lactic Acid): Synthesis, Structures, Properties, Processing, and Application John Wiley & Sons: Hobken 2010 one page.*
Physical Properties of Glycerine and its Solutions Gulf Publishing Company 1967 p. 1-27.*
Xanthan Gum MSDS 2008.*
Citric Acid MSDS 2002.*
Lee et al. Progress in Polymer Science 2012 37:106-126.*
Segeren et al. Faraday Discussions of the Chemical Society 1974 57:255-262.*

(Continued)

*Primary Examiner* — Robert A Wax
*Assistant Examiner* — Caralynne E Helm
(74) *Attorney, Agent, or Firm* — Mintz, Levin, Cohn, Ferris, Glovsky and Popeo, P.C.

(57) ABSTRACT

The present disclosure relates to compositions and methods for inhibiting inflammation and reducing the risk of spreading sexually transmitted diseases using an alginic acid-based antimicrobial compound. Such compositions provide dual protection by (1) attacking and inactivating viruses and other microbes and (2) blocking the host response that viruses trigger to invade host cells. Such compositions can also be part of an acid buffering contraceptive.

19 Claims, No Drawings

(56) References Cited

U.S. PATENT DOCUMENTS

| | | |
|---|---|---|
| 2015/0202216 A1 | 7/2015 | Guthrie |
| 2016/0008276 A1 | 1/2016 | Guthrie |
| 2016/0136193 A1 | 5/2016 | Hansen |
| 2017/0128396 A1 | 5/2017 | Guthrie |
| 2019/0133978 A1 | 5/2019 | Guthrie |
| 2020/0147015 A1 | 5/2020 | Guthrie |

FOREIGN PATENT DOCUMENTS

| | | | |
|---|---|---|---|
| EP | 0255902 A1 | 2/1988 | |
| JP | S6379816 A | 4/1988 | |
| JP | H02104517 A | 4/1990 | |
| JP | H06172375 A | 6/1994 | |
| JP | H10507178 A | 7/1998 | |
| JP | H11501292 A | 2/1999 | |
| JP | 3202365 B2 | 8/2001 | |
| JP | 2009102407 A * | 5/2009 | |
| JP | 6352907 B2 | 6/2018 | |
| KR | 1020100016060 A | 2/2010 | |
| RU | 2257197 C1 | 7/2005 | |
| WO | 9610989 A1 | 4/1996 | |
| WO | WO-199619195 | 6/1996 | |
| WO | WO-0138284 A1 | 5/2001 | |
| WO | WO-0166084 A2 | 9/2001 | |
| WO | WO-03000224 A1 | 1/2003 | |
| WO | WO-2004011032 A1 | 2/2004 | |
| WO | 2008119518 A1 | 10/2008 | |
| WO | WO-2009155118 A1 * | 12/2009 | A61M 31/002 |
| WO | 2010142761 A1 | 12/2010 | |
| WO | WO-2010138823 A1 | 12/2010 | |
| WO | WO-2012151237 A1 | 11/2012 | |
| WO | WO-2013187984 A1 | 12/2013 | |
| WO | WO-2015027071 A1 | 2/2015 | |
| WO | WO-2015095793 A1 | 6/2015 | |

OTHER PUBLICATIONS

Andrei et al. Topical tenofovir, a microbicide effective against HIV, inhibits herpes simplex virus-2 replication. Cell Host Microbe 10(4):379-389 (2011).

Asada et al. Inhibitory effect of alginic acids on hyaluronidase and on histamine release from mast cells. Biosci. Biotech. Biochem. 61(6):1030-1032 (1997).

Dien et al. Recombinant *Escherichia coli* engineered for production of L-lactic acid from hexose and pentose sugars. J Ind Microbiol Biotechnol 27(4):259-264 (2001).

Donati et al. Material Properties of Alginates. Alginates: Biology and Applications: Biology and Applications, Rehm, ed., Springer Dordrecht Heidelburg, London, UK, p. 10 (2009).

Flemming et al. The Crucial Role of Extracellular Polymeric Substances in Biofilms. Biofilms in Wastewater Treatment: An Interdisciplinary Approach, Wuertz, Bishop, Wilderer, eds., IWA Publishing, London, UK (pp. 181-187) (2003).

Ishida et al. Efficient production of L-Lactic acid by metabolically engineered *Saccharomyces cerevisiae* with a genome-integrated L-lactate dehydrogenase gene. Appl Environ Microbiol 71(4):1964-1970 (2005).

Jeong et al. Alginic acid has anti-anaphylactic effects and inhibits inflammatory cytokine expression via suppression of nuclear factor-kappaB activation. Clinical and Experimental Allergy 36:785-794 (2006).

O'Hanlon et al. In vaginal fluid, bacteria associated with bacterial vaginosis can be suppressed with lactic acid but not hydrogen peroxide. BMC Infect Dis 11:200 (2011).

Pande et al. Nuclear factor kappa B: a potential target for anti-HIV chemotherapy. Curr Med Chem 10(16):1603-1615 (2003).

PCT/US2014/071664 International Preliminary Report on Patentability dated Jun. 30, 2016.

PCT/US2014/071664 International Search Report and Written Opinion dated Apr. 17, 2015.

Purcell et al. Biology of mucosally transmitted sexual infection—translating the basic science into novel HIV intervention: a workshop summary. AIDS Res Hum Retroviruses 28(11):1389-1396 (2012).

Rehan et al. The semen of fertile men: statistical analysis of 1300 men. Fertil Steril 26:492-502 (1975).

The History of Alginate Chemistry—Bacterial. Cyber Colloids, LTD. Available at http://www.cybercolloids.net/information/technical-articles/history-alginate-chemistry-bacterial (1 pg.) (1978).

Urb et al. The Role of Mast Cells in the Defense against Pathogens. PLoS Pathog 8(4):e1002619 (2012).

Zhang, Tao, Timothy F. Sturgis, and Bi-Botti C. Youan. "pH-responsive nanoparticles releasing tenofovir intended for the prevention of HIV transmission." *European Journal of Pharmaceutics and Biopharmaceutics* 79.3 (2011): 526-536.

Owen, Derek H., et al, "Factors influencing nonoxynol-9 permeation and bioactivity in cervical mucus." Journal of controlled release 60.1 (1999): 23-34.

Centers for Disease Control and Prevention, Genital HPV infection—Fact sheet, 2020, 4 pages.

Proceedings of Symposium of the Japan Society for Bioscience, Biotechnology, and Agrochemistry, 2004:206 Pages.

(R)-9-(2-Phosphonomethoxypropyl)adenine, (R)-PMPA, CAS Registry No. 147127-20-6.

Draget et al. (2005) "Alginates from Algae", Peptide Science 6, 30 pages.

Leitch et al. (2002) "*Escherichia coli* O157 and Non-O157 Isolates are More Susceptible to L-Lactate than to D-Lactate", Applied and Environmental Microbiology, 68(9):4676-4678.

Malinova (2009) "Lactobor Intim Vaginal Gel for the Treatment and Prevention of Bacterial Vaginosis", Akush Ginekol (Sofiia) (English translation), 48(Suppl. 2):32-33.

Higgins (Oct. 2011) "L-lactate and D-lactate—Clinical Significance of the Difference", Acutecaretesting.org, 7 Pages.

Owen et al. (Jul.-Aug. 2005) "A Review of the Physical and Chemical Properties of Human Semen and the Formulation of a Semen Simulant", Journal of Andrology, 26(4):459-469.

* cited by examiner

COMPOSITIONS AND METHODS FOR INHIBITING INFLAMMATION AND DISEASES USING AN ALGINIC ACID-BASED ANTIMICROBIAL COMPOUND

CROSS REFERENCE TO RELATED APPLICATIONS

This application is the national phase entry of International application number PCT/US2014/071664, filed on Dec. 19, 2014, which claims the benefit U.S. provisional application No. 61/918,445, filed on Dec. 19, 2013, both of which are incorporated herein by reference in their entireties.

TECHNICAL FIELD

The present disclosure relates to compositions and methods for inhibiting inflammation and diseases, such as sexually transmitted diseases, using an alginic acid-based antimicrobial compound. Such compositions provide dual protection by (1) attacking and inactivating viruses and other microbes and (2) blocking the host response that viruses trigger to invade host cells. Such compositions can also be part of an acid buffering contraceptive.

BACKGROUND OF INVENTION

Sexually transmitted diseases (STDs) are illnesses that are transmitted between humans through sexual behavior. STDs can be caused by bacteria, viruses, protozoa, and parasites. While many STDs, especially those caused by bacteria, protozoa, and parasites can be cured with antibiotics or other medication, most STDs caused by viruses cannot be cured. Rather, drugs are used to keep the viral levels below levels which cause symptoms. Of the known viral STDs, the three most problematic are human immunodeficiency virus, hepatitis virus, and herpes simplex virus.

Human immunodeficiency virus (HIV), the etiologic agent of acquired immunodeficiency syndrome (AIDS) is the fastest growing cause of death in women of reproductive age. Worldwide, the heterosexual transmission of AIDS is the prevalent mode of transmission of AIDS, accounting for about 90% of all HIV infections in women. Therefore, significant attention has been directed to investigating measures that block sexual spreading of HIV infection. As there is no effective treatment or vaccine against AIDS, preventive measures are the primary tools that can presently reduce transmission of HIV. For example, the consistent and correct use of condoms represents an effective barrier to prevent HIV transmission. However, the risk of acquiring infection can only be significantly reduced if condoms are used for almost all sexual intercourse in HIV prevalent communities; a result that can not be achieved despite intensive prevention programs to increase condom use.

Hepatitis viruses cause inflammation of the liver. The most common hepatitis viruses are the five unrelated hepatotropic viruses, Hepatitis A (HAV), Hepatitis B (HBV), Hepatitis C (HCV), Hepatitis D (HDV), and Hepatitis E (HEV). The five hepatitis viruses are transmitted via either a fecal-oral route (hepatitis A and E) or via blood contact (hepatitis B, C, and D). HAV, HBV, and HEV can generally be cleared by the body's immune system. However, HCV and HBV can cause chronic hepatitis. HDV is unique in that it can only propagate in the presence of HBV. However, the presence of HDV exacerbates the symptoms of HBV. Proper condom use can help to prevent the transmission of HBV, HCV, and HDV.

Herpes simplex virus (HSV) belongs to a family of viruses, nine of which are known to cause diseases in humans. The nine human herpes viruses cause a variety of diseases including chicken pox, shingles, mononucleosis, sixth disease, and Kaposi's sarcoma. The HSV family includes two viruses, referred to as HSV-1 and HSV-2, that cause blisters in the skin or mucous membranes of the mouth, lips and/or genitals. While both viruses can infect either the mouth or genitals, HSV-1 predominantly infects orofacial tissue, whereas HSV-2 predominantly infects genital tissue. Both HSV-1 and HSV-2 are transmitted through close physical contact. The Center for Disease Control (CDC) estimates that one in six people aged 14-49 are infected with HSV-2. While condom use can reduce the risk of spreading HSV, however, HSV can still be transmitted via contact with genital skin that is not covered by the condom.

Significant emphasis has been placed on the development of intravaginal microbicidal agents capable of preventing and/or reducing the spread of a variety of STDs. The development of microbicides for topical use represents an important alternative to condom usage. A microbicide is any agent that kills or deactivates disease-causing microbes, including viruses. According to the International Association of Physicians in AIDS CARE (IAPAC), the definition of microbicides also includes interventions that can block or prevent infection, as well as amplification of the body's natural defenses to prevent infection through sexual acts.

Ideally, microbicides should have little or no side effects at an effective microbicidal concentration. Accordingly, the drug used as a microbicide should have little or no immunosuppressive activity at an effective microbicidal concentration. In addition, the ideal microbicide should sufficiently withstand varying temperatures and acceptably function within varied pH ranges (ranges of alkaline and acidic levels in the vagina). Further, it should not eliminate the natural beneficial lactobacilli that reside in the vagina and contribute to vaginal health.

Topical microbicides would be even more beneficial if they also had contraceptive capabilities. Contraception is also important for women with STDs to prevent transmitting diseases to future generation, especially since many women with STDs are of childbearing age. At present, a majority of commercially available dual-purpose spermicidal microbicides have detergent ingredients that disrupt cell membranes. The most widely used vaginal spermicide, nonoxynol-9 (N-9), because of its membrane disruptive properties, has been shown to damage the cervicovaginal epithelium, cause an acute inflammatory tissue response, alter vaginal microflora, and enhance the risk of promoting opportunistic infections in the genitourinary tract. N-9 is also toxic to vaginal and cervical cells which increases the permeability of vaginal tissue. It can also kill the *Lactobacillus* sp. that populate the vaginal tract and are generally regarded as beneficial. *Lactobacillus* produce lactic acid and hydrogen peroxide, which helps maintain the acidic pH of the vagina (~pH 3.5 to 5.0) and a healthy vaginal flora. At this pH, a number of STD-causing organisms like HIV are inactivated.

Other microbicides in the form of vaginal creams and ointments are currently available over the counter or by prescription. Still others are in various stages of development. Examples include octoxynol-9 and benzalkonium chloride. Gels designed to control vaginal pH are also available, such as AciJel™ (Ortho-McNeil Pharmaceutical Corp., Raritan, N.J.) which is a water dispersible buffered gel having a pH of 3.9 to 4.1. It is used to restore and maintain normal vaginal acidity. Such gels are designed to control vaginal pH and are not specifically designed to prevent STDs and/or contraception, and thus do not always possess effective microbicidal activity.

As discussed, presently marketed vaginal contraceptive compositions, often containing N-9 as an active ingredient, are generally known in the art. While presently marketed vaginal contraceptive formulations aid in preventing pregnancy, their ability to effectively prevent STDs, particularly HIV/AIDS, is very limited. Moreover, recent analyses show that N-9, when used frequently by women at high risk may actually increase the risk of HIV infection (WHO 2002, WHO/CONRAD technical consultation on nonoxynol-9, Geneva).

Additionally, several microbicides under development contain anti-retroviral agents that had originally been developed for the treatment of patients with HIV infection. However, only temporary and limited benefits are observed in HIV-infected patients treated with any of the actual anti-retrovirals or combinations thereof. The limited ability of these agents to decrease viral burden, the rapid development of resistance and the toxic side-effects of most drugs has limited their long-term efficacy. One major problem associated with the administration of antiviral agents to patients is their poor ability to penetrate and target infected cells. Rapid drug clearance and the toxicity of parent compounds or metabolites also constitute some of the major drawbacks that may slow down the development and use of many antiviral agents. Given the severe toxicity of antiviral agents actually available to treat AIDS and other viral diseases and their limited ability to target infected cells, strategies aimed at reaching therapeutic levels of drugs into infected cells and reducing toxicity is needed.

Recent studies have shown that a significant contribution to the antimicrobial properties naturally present in the vagina is primarily due to the microbicidal activity of the lactic acid molecule, and is not necessarily due to low pH alone or to the presence of hydrogen peroxide. (O'Hanlon et al., BMC Infect Dis., 11:200, 2011). In particular, it has been shown that in vaginal fluid, bacteria associated with bacterial vaginosis can be suppressed with lactic acid, but to a much lesser extent with other acids at the same pH.

Accordingly, there is a need for an alternative easy to use STD inhibitor that effectively reduces the risk of transmission of viral-based STDs. Such compositions should be useful for vaginal administration in effective doses that do not inactivate *Lactobacillus* sp. or cause overt vaginal irritation or other toxicity. The compositions would be even more beneficial if they also had contraceptive capabilities.

SUMMARY OF INVENTION

The embodiments disclosed below satisfy this need. The following simplified summary is provided in order to establish a basic understanding of some aspects of the claimed subject matter. This summary is not an extensive overview, and is not intended to identify key/critical elements or to delineate the scope of the claimed subject matter.

One embodiment is a composition for inhibiting the transmission of diseases. The composition includes 1-(6-aminopurin-9-yl)propan-2-yloxymethylphosphonic acid (tenofovir) or a physiologically functional derivative thereof, alginic acid polymer, and an aqueous based carrier. An exemplary alginic acid polymer of the present disclosure have an average molecular weight between about 20,000 to about 400,000 and a ratio of mannuronate:guluronate residues in the polymer between about 0.25 to about 2.0. In another embodiment the ratio of mannuronate:guluronate residues in the alginic acid polymer is between 0.3 to 1.5. In another embodiment the ratio of mannuronate:guluronate residues in the alginic acid polymer is between 0.3 to 1. In another embodiment the ratio of mannuronate:guluronate residues in the alginic acid polymer is between 0.3 to 0.8. In another embodiment the ratio of mannuronate:guluronate residues in the alginic acid polymer is between 0.3 to 0.6. In another embodiment, the ratio of mannuronate:guluronate residues in the alginic acid polymer is about 0.2, 0.25, 0.3, 0.35, 0.4, 0.45, 0.5, 0.55, 0.6, 0.65, 0.7, 0.75, 0.8, 0.85, 0.9, 0.95, 1, 1.05, 1.1, 1.15, 1.2, 1.25, 1.3, 1.35, 1.4, 1.45, 1.5, 1.55, 1.6, 1.65 1.7, 1.75, 1.8, 1.85, 1.9, 1.95, or 2.0. In another embodiment, the average molecular weight of the alginic acid is between 75,000 to 375,000. In another embodiment, the average molecular weight of the alginic acid is between 100,000 to 300,000. In another embodiment the average molecular weight of the alginic acid is between 100,000 to 200,000. In another embodiment, the average molecular weight of the alginic acid is between 125,000 to 175,000. In another embodiment, the average molecular weight of the alginic acid is at least 20,000. In another embodiment, the average molecular weight of the alginic acid is at least 50,000. In another embodiment, the average molecular weight of the alginic acid is at least 75,000. In another embodiment, the average molecular weight of the alginic acid is at least 100,000. In another embodiment, the average molecular weight of the alginic acid is at least 125,000. In another embodiment, the average molecular weight of the alginic acid is at least 150,000.

In another embodiment, the composition also includes lactic acid. In another embodiment, the lactic acid is the "L" form of lactic acid. In another embodiment, the composition also includes pamoic acid or a salt or ester thereof. In yet another embodiment, the composition also includes carrageenan. In yet another embodiment, the carrageenan is iota carrageenan. In yet another embodiment, the composition may also include a buffering agent (such as citric acid, potassium acid tartrate, sorbic acid, fumaric acid, ascorbic acid, stearic acid, oleic acid, tartaric acid, potassium bitartrate, edetic acid ethylenediaminetetracetic acid, acetic acid, malic acid, and the like), thickener (such as xanthan gum, hydroxypropyl cellulose, hydroxypropyl methyl cellulose, sodium carboxymethyl cellulose, chitosan, polycarbophil, carbopol, gellan gum, poloxamer, carrageenan, iota carrageenan, and the like), humectant (such as glycerol, polyethylene glycols, propylene glycols, sorbitol, triacetin, and the like), or preservative (such as benzoic acid, sodium benzoate, methylparaben, ethylparaben, butylparaben, propylparaben, benzyalkonium chloride, phenylmercuric nitrate, chlorhexidine, and the like). In yet another embodiment, the carrier of the composition is water.

Another embodiment is an acid buffering contraceptive. The acid buffering contraceptive includes alginic acid, a bioadhesive compound, and lactic acid in a pharmaceutically acceptable carrier. The alginic acid has an average molecular weight between 20,000 to 400,000 and a ratio of mannuronate:guluronate residues between 0.25 to 2.0. In another embodiment the mannuronate:guluronate residues is between 0.3 to 1.5. In another embodiment the mannuronate:guluronate residues is between 0.3 to 1. In another embodiment, the mannuronate:guluronate residues is between 0.3 to 0.8. In another embodiment, the mannuronate:guluronate residues is between 0.3 to 0.6. In another embodiment, the ratio of mannuronate:guluronate residues in the alginic acid polymer is about 0.2, 0.25, 0.3, 0.35, 0.4, 0.45, 0.5, 0.55, 0.6, 0.65, 0.7, 0.75, 0.8, 0.85, 0.9, 0.95, 1, 1.05, 1.1, 1.15, 1.2, 1.25, 1.3, 1.35, 1.4, 1.45, 1.5, 1.55, 1.6, 1.65 1.7, 1.75, 1.8, 1.85, 1.9, 1.95, or 2.0. In another embodiment, the average molecular weight of the alginic acid is between 75,000 to 375,000. In another embodiment, the average molecular weight of the alginic acid is between 100,000 to 300,000. In another embodiment the average molecular weight of the alginic acid is between 100,000 to 200,000. In another embodiment, the average molecular weight of the alginic acid is at least 50,000. In another embodiment, the average molecular weight of the alginic acid is at least 75,000. In another embodiment, the average molecular weight of the alginic acid is at least 100,000. In another embodiment, the average molecular weight of the alginic acid is at least 125,000. In another embodiment, the average molecular weight of the alginic acid is at least 150,000. Using the above described alginic acids may further enhance the ability of the acid buffering contraceptive to inhibit the transmission of diseases.

In one embodiment, the bioadhesive compound of the acid buffering contraceptive may be xanthan gum, carrageenan, iota carrageenan, hydroxypropyl cellulose, hydroxypropyl methyl cellulose, sodium carboxymethyl cellulose, chitosan, polycarbophil, carbopol, and the like. In another embodiment, the acid buffering compound may also include buffering agents (such as citric acid, potassium acid tartrate, sorbic acid, fumaric acid, ascorbic acid, stearic acid, oleic acid, tartaric acid, potassium bitartrate, edetic acid ethylenediaminetetracetic acid, acetic acid, malic acid, and the like), thickeners (such as xanthan gum, hydroxypropyl cellulose, hydroxypropyl methyl cellulose, sodium carboxymethyl cellulose, chitosan, polycarbophil, carbopol, gellan gum, poloxamer, carrageenan, iota carrageenan, and the like), humectants (such as glycerol, polyethylene glycols, propylene glycols, sorbitol, triacetin, and the like), preservatives (such as benzoic acid, sodium benzoate, methylparaben, ethylparaben, butylparaben, propylparaben, benzyalkonium chloride, phenylmercuric nitrate, chlorhexidine, and the like), or agents that enhance drug solubility, permeability and absorption (such as pamoic acid and salts and esters thereof). In another embodiment, the lactic acid is L-lactic acid.

In one embodiment, the acid buffering contraceptive includes alginic acid, xanthan gum, and lactic acid. In another embodiment, the acid buffering contraceptive includes alginic acid, carrageenan, and lactic acid. In another embodiment, the acid buffering contraceptive includes alginic acid, iota carrageenan, and lactic acid. In yet another embodiment, the acid buffering contraceptive includes alginic acid, xanthan gum, pamoic acid, and lactic acid. In another embodiment, the acid buffering contraceptive includes alginic acid, carrageenan, pamoic acid, and lactic acid. In another embodiment, the acid buffering contraceptive includes alginic acid, iota carrageenan, pamoic acid, and lactic acid.

In another embodiment, the acid buffering contraceptive may also include a buffering agent (such as citric acid, potassium acid tartrate, benzoic acid, sorbic acid, fumaric acid, ascorbic acid, stearic acid, oleic acid, tartaric acid, potassium bitartrate, edetic acid ethylenediaminetetracetic acid, acetic acid, malic acid, and the like), thickener (such as xanthan gum, hydroxypropyl cellulose, hydroxypropyl methyl cellulose, sodium carboxymethyl cellulose, chitosan, polycarbophil, carbopol, gellan gum, poloxamer, carrageenan, iota carrageenan, and the like), humectant (such as glycerol, polyethylene glycols, propylene glycols, sorbitol, triacetin, and the like), or preservative (such as benzoic acid, sodium benzoate, methylparaben, ethylparaben, butylparaben, propylparaben, benzyalkonium chloride, phenylmercuric nitrate, chlorhexidine, and the like). In yet another embodiment, the carrier of the composition is water.

Another embodiment is an acid buffering contraceptive. The acid buffering contraceptive includes 1-(6-aminopurin-9-yl)propan-2-yloxymethylphosphonic acid (tenofovir) or a physiologically functional derivative thereof, alginic acid, a bioadhesive compound, and lactic acid in a pharmaceutically acceptable carrier. The alginic acid has an average molecular weight between 20,000 to 400,000 and a ratio of mannuronate:guluronate residues between 0.25 to 2.0. In another embodiment the mannuronate:guluronate residues is between 0.3 to 1.5. In another embodiment the mannuronate:guluronate residues is between 0.3 to 1. In another embodiment, the mannuronate:guluronate residues is between 0.3 to 0.8. In another embodiment, the mannuronate:guluronate residues is between 0.3 to 0.6. In another embodiment, the ratio of mannuronate:guluronate residues in the alginic acid polymer is about 0.2, 0.25, 0.3, 0.35, 0.4, 0.45, 0.5, 0.55, 0.6, 0.65, 0.7, 0.75, 0.8, 0.85, 0.9, 0.95, 1, 1.05, 1.1, 1.15, 1.2, 1.25, 1.3, 1.35, 1.4, 1.45, 1.5, 1.55, 1.6, 1.65 1.7, 1.75, 1.8, 1.85, 1.9, 1.95, or 2.0. In another embodiment, the average molecular weight of the alginic acid is between 75,000 to 375,000. In another embodiment, the average molecular weight of the alginic acid is between 100,000 to 300,000. In another embodiment the average molecular weight of the alginic acid is between 100,000 to 200,000. In another embodiment, the average molecular weight of the alginic acid is at least 50,000. In another embodiment, the average molecular weight of the alginic acid is at least 75,000. In another embodiment, the average molecular weight of the alginic acid is at least 100,000. In another embodiment, the average molecular weight of the alginic acid is at least 125,000. In another embodiment, the average molecular weight of the alginic acid is at least 150,000. Using the above described alginic acids may further enhance the ability of the acid buffering contraceptive to inhibit the transmission of diseases.

In one embodiment, the bioadhesive compound of the acid buffering contraceptive with tenofovir may be xanthan gum, carrageenan, iota carrageenan, hydroxypropyl cellulose, hydroxypropyl methyl cellulose, sodium carboxymethyl cellulose, chitosan, polycarbophil, carbopol, and the like. In another embodiment, the acid buffering compound may also include buffering agents (such as citric acid, potassium acid tartrate, sorbic acid, fumaric acid, ascorbic acid, stearic acid, oleic acid, tartaric acid, potassium bitartrate, edetic acid ethylenediaminetetracetic acid, acetic acid, malic acid, and the like), thickeners (such as xanthan gum, hydroxypropyl cellulose, hydroxypropyl methyl cellulose, sodium carboxymethyl cellulose, chitosan, polycarbophil, carbopol, gellan gum, poloxamer, carrageenan, iota carrageenan, and the like), humectants (such as glycerol, polyethylene glycols, propylene glycols, sorbitol, triacetin, and the like), preservatives (such as benzoic acid, sodium benzoate, methylparaben, ethylparaben, butylparaben, propylparaben, benzyalkonium chloride, phenylmercuric nitrate, chlorhexidine, and the like), or agents that enhance drug solubility, permeability and absorption (such as pamoic acid and salts and esters thereof). In another embodiment, the lactic acid is L-lactic acid.

In one embodiment, the acid buffering contraceptive with tenofovir includes alginic acid, xanthan gum, and lactic acid. In another embodiment, the acid buffering contraceptive includes alginic acid, carrageenan, and lactic acid. In another embodiment, the acid buffering contraceptive includes alginic acid, iota carrageenan, and lactic acid. In yet another embodiment, the acid buffering contraceptive includes alginic acid, xanthan gum, pamoic acid, and lactic acid. In another embodiment, the acid buffering contraceptive includes alginic acid, carrageenan, pamoic acid, and lactic acid. In another embodiment, the acid buffering contraceptive includes alginic acid, iota carrageenan, pamoic acid, and lactic acid.

In another embodiment, the acid buffering contraceptive with tenofovir may also include a buffering agent (such as citric acid, potassium acid tartrate, benzoic acid, sorbic acid, fumaric acid, ascorbic acid, stearic acid, oleic acid, tartaric acid, potassium bitartrate, edetic acid ethylenediaminetetracetic acid, acetic acid, malic acid, and the like), thickener (such as xanthan gum, hydroxypropyl cellulose, hydroxypropyl methyl cellulose, sodium carboxymethyl cellulose, chitosan, polycarbophil, carbopol, gellan gum, poloxamer, carrageenan, iota carrageenan, and the like), humectant (such as glycerol, polyethylene glycols, propylene glycols, sorbitol, triacetin, and the like), or preservative (such as benzoic acid, sodium benzoate, methylparaben, ethylparaben, butylparaben, propylparaben, benzyalkonium chloride, phenylmercuric nitrate, chlorhexidine, and the like). In yet another embodiment, the carrier of the composition is water.

Another embodiment is a method for reducing the risk of spreading a sexually transmitted disease by topically administering an effective amount of any of the compositions described above and herein. In another embodiment, the compositions may be topically applied to the vagina, cervix, mouth, anus, and/or rectum. The compositions may be applied before sexual activity. In one embodiment, the compositions may be applied at least 15 minutes or at least 30 minutes or at least 1 hour or at least 1.5 hours or at least 2 hours or at least 2.5 hours or at least 3 hours or at least 3.5 hours or at least 4 hours or at least 4.5 hours or at least 5 hours or at least 6 hour or at least 7 hours or at least 8 hours or at least 9 hours or at least 10 hours or at least or at least 12 hours prior to sexual activity. The compositions may also be applied after sexual activity. In one embodiment, the compositions may be applied immediately after or within 5 minutes after or within 10 minutes after or within 15 minutes after or within 20 minutes after or within 30 minutes after or within 45 minutes after or within 1 hour after, or within 2 hours after or within 3 hours after or within 4 hours after or within 5 hours after or within 6 hours after or within 7 hours after or within 8 hours after or within 9 hours after or within 10 hours after sexual activity. In another embodiment, the compositions may be applied to the surface of a physical barrier device such as a condom, sponge, or diaphragm before using the barrier device.

In another embodiment are methods for manufacturing the compositions described herein. In one embodiment, the 1-(6-aminopurin-9-yl)propan-2-yloxymethylphosphonic acid (tenofovir) or a physiologically functional derivative thereof is dissolved in a basic solution. Once the tenofovir is dissolved, the solution is brought to below neutral and alginic acid is added. In one embodiment, the pH of the solution is reduced with the addition of lactic acid. In another embodiment, additional additives are added based on the pH of the additive. For example, buffering agents may be used to reduce the pH of the solution, i.e. make it more acidic. In another embodiment, thickeners may be added. In some methods, thickeners may be added last since the addition of thickeners may inhibit the incorporation of some ingredients.

In another embodiment are kits containing the above described compositions in an easy to dispense container. Non-limiting examples of dispensing containers include a bottle, tube, a syringe, a suppository, or a pump. The kit may also contain a device for applying the compositions to the desired surface and/or instructions for use or application. Non-limiting applicator devices include a syringe, a sponge, a brush, a swab, or a spatula. In one embodiment, the compositions may be portioned out in single use doses. Non-limiting examples include pre-filled syringes, pre-filled squeeze tubes, or suppositories. In another embodiment, the composition may be coated on barrier devices. Non-limiting examples of barrier devices include sponges, condoms or diaphragms.

Other aspects of the disclosure are found throughout the specification.

DETAILED DESCRIPTION OF INVENTION

Disclosed herein are compositions and methods for inhibiting inflammation and reducing the risk of spreading sexually transmitted diseases (STDs) using an alginic acid-based antimicrobial compounds. Such compositions provide a dual protection by (1) attacking and inactivating viruses and other microbes and (2) blocking the host response that viruses activate to facilitate host cell invasion. More specifically, the compositions and methods disclosed herein relate to synergistic compositions comprising a combination of alginic acid and an antiviral agent in a carrier that enhances the efficacy of the individual components. The alginic acid-based antimicrobial compounds can also be part of an acid buffering contraceptive.

To facilitate understanding of the disclosure that follows, a number of terms are defined below.

When the terms "one," "a," or "an" are used in this disclosure, they mean "at least one" or "one or more," unless otherwise indicated.

As used herein, the terms "antimicrobial," "microbicide," and "microbicidal" refer to a compound capable of preventing or inhibiting the growth and/or preventing or reducing the infectivity of microbes, including viruses, bacteria, fungi, protozoa, parasites, and algae.

As used herein, the term "sexually transmitted disease" is used interchangeably with "STD," "sexually transmitted infection," "STI" and/or the plural thereof. An STD is an illness or pathophysiological condition that has a significant probability of transmission between humans by means of any form of sexual contact, including kissing. The term STD may also encompass a person who is infected, and may potentially infect others, without showing signs of disease or infection.

The terms "synergy" and "synergistic" mean that the effect achieved with the compounds used together is greater than the sum of the effects that results from using the compounds separately, i.e. greater than what would be predicted based on the two active ingredients administered separately. A synergistic effect may be attained when the compounds are: (1) co-formulated and administered or delivered simultaneously in a combined formulation; (2) delivered by alternation or in parallel as separate formulations; or (3) by some other regimen. A synergistic antiviral effect denotes an antiviral effect which is greater than the predicted purely additive effects of the individual compounds of the combination.

As used herein, the term "physiologically functional derivative" refers to a pharmaceutically active compound with equivalent or near equivalent physiological functionality to tenofovir when administered in combination with another pharmaceutically active compound in a combination of the disclosure. As used herein, the term "physiologically functional derivative" includes any: physiologically acceptable salt, ether, ester, prodrug, solvate, stereoisomer including enantiomer, diastereomer or stereoisomerically enriched or racemic mixture, and any other compound which upon administration to the recipient, is capable of providing (directly or indirectly) such a compound or an antiviral-active metabolite or residue thereof.

As used herein, the term "contacting" refers to any suitable method of bringing one or more of the alginic acid-based compounds described herein into contact with a sexually-transmitted or sexually-acquired microbe or microbial cell, as described herein. In vitro or ex vivo, this is achieved by exposing the microbe or microbial cell to the microbicide in a suitable medium. For exemplary in vivo applications, topical methods of administration are suitable as described herein.

As used herein, the term "matrix" is meant to refer to a plurality of different molecules that form a three-dimensional structure via ionic interactions there between.

The term "buffering capabilities" means the ability to maintain a desired pH when contacted with a compound having a different pH. In particular, buffering capabilities means the ability to maintain a healthy vaginal pH.

The term "contacted with ejaculate" means the presence of semen in the volume normally occurring during ejaculation, e.g., between 0.1 to 11 milliliters (Rehan, et al., Fertil Steril. 1975, 26:492-502).

The term "basic solution" means a solution that has a pH above 7, such as 8, 9, 10, 11, 12, or 13. Exemplary bases for making a "basic solution" include, but are not limited to, sodium hydroxide, potassium hydroxide, and lithium hydroxide.

The term "inhibiting disease" as used herein generally refers to the inhibition of sexually transmitted diseases, which includes inhibiting the spread thereof.

The term "alginic acid" or "alginic acid polymer" or "alginate" are used interchangeably and refer to a polysaccharide polymer of beta-D-mannuronate and alpha-L-guluronate.

The alginic acid-based microbicide compositions and methods disclosed herein prevent or reduce the risk of the transmission of STDs and/or common vaginal infections. STDs include, but are not limited to, HIV/AIDS, herpes (caused by herpes simplex virus type 1 (HSV-1) or herpes simplex virus type 2 (HSV-2), hepatitis, gonorrhea, chlamydia, syphilis, and trichomoniasis. Non-limiting examples of common vaginal infections include bacterial vaginosis (BV) and vaginal candidiasis. Similar compositions and methods of application of such compositions, as described herein, can be used for preventing or treating STDs and/or common vaginal infections. Additional chemicals may be added to the alginic acid-based microbicide compositions to form an acid buffering contraceptive.

The compositions of the present disclosure comprise a combination of an alginic acid polymer and a particular antiviral agent, tenofovir. Alginic acid is an acidic polymer that (1) has mucosal adhesive and bioadhesive properties that provide a physical barrier, (2) has buffering capabilities to help maintain an acidic environment in the vagina, and (3) has anti-inflammatory properties that reduce viral infection in host cells. Tenofovir is an antiretroviral drug designed to inhibit reverse transcriptase. The prodrug form of tenofovir, tenofovir disproxyl fumarate, has been approved by the U.S. Food and Drug Administration for treating HIV and chronic hepatitis B and may be effective against other viruses such as herpes. (Andrei, et al., Cell Host Microbe., 10:379-89, 2011). In exemplary embodiments, a synergistic effect is achieved between the alginic acid polymer and antiviral agent. More particularly, the negatively charged monophosphate moiety of tenofovir forms ionic interactions with the alginic acid polymer, facilitating prolonged release of the tenofovir, thus enhancing efficacy. In other embodiments, the alginic acid polymer and tenofovir can be combined with lactic acid, and a bioadhesive such as xanthan gum or carrageenan to form an acid buffering contraceptive. The acid buffering contraceptive forms a matrix upon contact with ejaculate that traps sperm and other microbes present in ejaculate.

Though not wishing to be bound by any particular theory of operation, it is further believed that the compositions of the present disclosure exhibit improved efficacy because the tenofovir concentration is maintained between effective and toxic levels, by way of alginic acid's mucoadhesive and bioadhesive properties that inhibit the dilution of the antiretroviral drug away from the delivery point, thereby improving targeting and localization of the drug. In this context, mucoadhesion and bioadhesion increases the intimacy and duration of contact between the tenofovir and the mucosal surface. The combined effects of this enhanced, direct drug absorption, and the decrease in excretion rate that results from reduced diffusion and improved localization significantly enhances bioavailability of the drug and allows for a smaller dosage and less frequent administration.

Microbial Infection and Inflammation

Toll-like receptors (TLRs) are the immune systems' early warning sign against exposure to potentially harmful substances, especially chemicals derived from microbes. Specifically, TLRs bind to molecular structures called pathogen-associated molecular patterns (PAMPs) that are present in bacteria, protozoa, fungi, and viruses. Upon activation, TLRs trigger multiple biochemical cascades that activate inflammation and cellular immune defenses, including nuclear factor kappa-light-chain-enhancer of activated B cells (NFkB). NFkB is the master gene regulator of inflammation, activation of which results in the increased synthesis of many inflammatory mediatory and pro-inflammatory cytokines, including TNF-alpha, IL-1, and other interleukins. For many viruses, activation of the inflammatory pathways that typically aid in immune defense against microbial infection, instead, enhance infectivity. It is now known that certain viruses, including HIV, hepatitis, and HSV, require the activation of NFkB to infect the host cell. For example, upon activation, NFkB binds to a site on the HIV long terminal repeat to start transcription of integrated HIV genome. (See Pande and Ramos, Curr. Med. Chem., vol. 10, no. 16, pgs. 1603-15 (2003).) In effect, the body's own natural response is contributing to the infectivity of the virus.

Physical Trauma and Inflammation

Many sexual activities result in physical trauma to the tissues on a microscopic level. Upon disruption of an anatomical barrier, e.g. mucous membranes, neutrophils are attracted by a variety of cytokines released by inflammatory cells such as mast cells. Neutrophils engulf damaged cells by phagocytosis and in the process, generate and release high quantities of reactive oxygen species (ROS) that are toxic to healthy surrounding cells. ROS react with cellular antioxidants, in particular, glutathione. Upon exposure to ROS, reduced glutathione (GSH) shifts to its oxidized state (GSSG). Increased cellular levels of oxidized glutathione triggers activation of NFkB. As mentioned above, activation of NFkB facilitates infection of viral STDs.

Alginic Acid

Alginates are naturally occurring polymers that can be extracted from brown algae. The polymer is made up of two sugars, 1,4-linked β-D-mannuronate (M) and α-L-guluronate (G). The polymers can be made up of blocks of consecutive M residues, blocks of consecutive D residues, or alternative D and M residues. The ratio of M:G varies depending on the source. Most commercially available alginates have a G content between 14-31%, however, alginates from *Laminaria* hyperborean have a G content of 60%. Alginates with a more defined chemical structure and physical properties can be obtained using bacterial biosynthesis. However, bacterial alginates have an O-acetyl group at C2 and/or C3. Acetyl groups are exclusively associated with the mannuronic acid residues with degrees of acetylation varying from 4-57%. (See Donati and Paoletti, "Material Properties of Alginates," in *Alginates: Biology and Applications: Biology and Applications*, Rehm, ed., Springer Dordrecht Heidelburg, London, UK, 2009, page 10 and "The History of Alginate Chemistry Bacterial," Cyber Colloids, LTD, www.cybercolloids.net/information/technical-articles/history-alginate-chemistry-bacterial.) Acetyl groups decrease the capacity and selectivity of cation binding, increase solution viscosity, enhance water holding capacity, and protect degradation by alginate lyases. (See Flemming and Wingender, "The Crucial Role of Extracellular Polymeric Substances in Biofilms," in *Biofilms in Wastewater Treatment: An Interdisciplinary Approach*, Wuertz, Bishop, Wilderer, eds., IWA Publishing, London, UK 2003, page 184.) Alginates are typically extracted from brown algae using alkali solutions and salt to form alginate salts. Alginate salts can further be treated with acid to form alginic acid.

Alginates, like polysaccharides in general, are polydisperse with respect to molecular weight. Because of this polydispersity, the "molecular weight" of an alginate is an average over the whole distribution of molecular weights. (See Draget, et al., "Alginates From Algae," Biopolymers Online, DOI: 10.1002/3527600035.bpo16008 (2005).) The molecular-weight distribution can have implications for the uses of alginates, as low-molecular-weight fragments containing only short G-blocks may not take part in gel-network formation and consequently do not contribute to the gel strength. The molecular weight of most alginate salts is in the range of about 10,000 to 600,000 grams per mole (g/mol).

Alginate polymers can be cross-linked to form a hydrogel using monovalent and divalent cations such as calcium, sodium, and potassium. However, only the G residues are believed to participate when using divalent cations. Thus, the M:G ratio of the alginate affects the physical properties of alginate hydrogels. Furthermore, gelling time and temperature also affect gel uniformity and strength when using cations. Slow gelling rates (e.g. greater than 15 minutes) at lower temperatures (e.g. below body temperature) result in gels with more uniform structures and greater mechanical integrity. (See Asada, et al., Biosci. Biotech. Biochem., vol. 61, no. 6, pgs. 1030-1032 (1997).)

Both the M and G sugar residues contain carboxyl groups with pKa's around 3.5. At physiological pH, the carboxyl groups are ionized, forming long chains of repeating negatively-charge carboxyl groups that can hydrogen bond to water to form a thick tissue-adherent gel, e.g. bioadhesive. Alginates also adhere to mucosal surfaces using hydrogen bonding. It is believed that alginates can act as an "artificial mucosa" that protects against both chemical and physical trauma. Due to the innate mucoadhesive and bioadhesive properties of alginic acid, it should remain within the vagina for about 12 to 24 hours (or even longer) if not removed by the woman.

Alginates have anti-inflammatory capabilities. Specifically, studies have shown that alginic acid inhibits NFkB activation. NFkB is a protein complex that controls the transcription of DNA. (Sec Jcong, et al., Clinical and Experimental Allergy, vol. 36, pgs. 785-794 (2006).) NFkB is involved in cellular responses to stimuli such as stress, cytokincs, free radicals, ultraviolet irradiation, oxidized LDL, and bacterial or viral antigens. NFkB plays a key role in regulating the immune response to infection. It is now known that many viruses, including HIV, hepatitis, and herpes, activate NFkB to facilitate host cell infection. By preventing the activation of NFkB and, by extension, preventing the activation of multiple inflammatory pathways, alginic acid reduces the risk of viral STD infection.

Alginates also inhibit immunoglobulin E-mediated mast cell degranulation. (See Asada, et al., Biosci. Biotech. Biochem., vol. 61, no. 6, pgs. 1030-1032 (1997).) Mast cells play an important role in defense against pathogens. Pathogens can activate mast cells through stimulation of the immunoglobulin E (IgE) receptor or through pattern recognition receptor, which include toll-like receptors (TLRs), Nod-like receptors, C-type lectins, and the glycosylphosphatidylinositol-anchored protein CD48. Upon activation, mast cells release various mediators that affect vascular permeability and trigger additional immune responses. The mediators include granule-associated mediators, including histamine, serotonin, heparin, tryptase, chymase, and tumour necrosis factor-alpha, cytokines, and chemokines. In mucosal tissue, which can be the primary site for HIV infection, activation of mast cells, which leads to increased vascular permeability and mast cell interaction with T-cells may contribute to HIV infectivity. Furthermore, in HIV infection, mast cells may serve as a viral reservoir during latent infection and can be reactivated through TLR-mediated signals. (See Urb M and Sheppard, DC (2012) "The Role of Mast Cells in the Defence against Pathogens." PLoS Pathog 8(4): e1002619. doi:10.1371/journal.ppat. 1002619.)

It has been unexpectedly discovered that not all molecular weights of alginic acid are affective at blocking inflammation. Specifically alginates with molecular weights between 20,000 to 400,000 g/mol display greater capabilities in inhibiting mast cell degranulation. In one embodiment, the molecular weight of the alginate may be between 100,000 to 375,000 g/mol. In another embodiment, the molecular weight of the alginate may be between 200,000 and 350,000 g/mol. In yet another embodiment, the molecular weight of the alginate may be between 290,000 and 340,000 g/mol. (See Asada, et al., Biosci. Biotech. Biochem., vol. 61, no. 6, pgs. 1030-1032 (1997).)

It has also been unexpectedly discovered that the M:G ratio also affects the anti-inflammatory properties of alginic acid. In one embodiment, the M:G ratio may be between 0.25 and 2.0. In another embodiment, the M:G ratio may be between 0.3 and 1.5. In another embodiment, the M:G ration is between 0.5 and 1.2. In yet another embodiment, the M:G ratio is 1. (See Asada, et al., Biosci. Biotech. Biochem., vol. 61, no. 6, pgs. 1030-1032 (1997), incorporated by reference herein. Asada describes the 0.6 type sodium alginate as having an M:G ratio of 3:7, see second paragraph of article, however, an M:G ration of 3:7 mathematically is 0.43)

As noted above, alginates cross-link in the presence of monovalent and divalent cations such as sodium, potassium, and calcium. Vaginal fluids generally contain very little amounts of these cations. Semen, on the other hand, is abundant in these cations. Thus, in the presence of semen, alginic acid will cross-link to form a matrix that can trap sperm and microbes. Trapping sperm and other microbes present in semen will reduce the risk of transmission of STDs. Additionally, alginic acid has a pH of about 1.5 to 3.5 in an aqueous solution. Though not wishing to be bound by any particular theory of operation, the naturally low pH of alginic acid may help in maintaining a healthy vaginal pH (i.e. between 3.5 to 5.0). As noted above, a low pH inactivates many STD-causing microbes. Furthermore, alginic acid has bioadhesive and mucoadhesive properties which will keep the alginic acid-based compositions in place during sexual activity. Lastly, alginic acid is generally not absorbed by the body due to its high molecular weight.

Tenofovir

Tenofovir, which includes derivatives, analogues, prodrugs and salts thereof, belongs to a class of antiretroviral drugs known as nucleotide analogue reverse transcriptase inhibitors (NtRTIs), which block reverse transcriptase. It has the chemical name 1-(6-aminopurin-9-yl)propan-2-yloxymethylphosphonic acid [CAS Registry number: 147127-20-6]. Tenofovir is commercially available, such as from Gilead Sciences, Inc., (Foster City, Calif.).The structure of tenofovir is shown below:

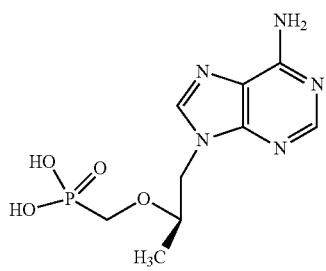 [SMILES: C[C@H](Cn1cnc2c(N)ncnc21)OCP(=O)(O)O]

Tenofovir is a competitive inhibitor of other naturally occurring nucleotides, and its ultimate biological activity is viral DNA chain termination. Tenofovir is a novel nucleotide analog with antiviral activity against both HIV and Hepatitis B. The mechanism of tenofovir is similar to that of nucleoside analogs, which interfere with reverse transcriptase and prevents translation of viral genetic material into viral DNA. Unlike the nucleoside analogs, the NtRTIs are chemically pre-activated with the presence of a phosphate group. Since the phosphorylation step is not necessary, nucleotide analogs can incorporate into viral DNA chain more rapidly than nucleoside analogs. More importantly, this will bypass a viral mechanism of nucleoside resistance.

Acid Buffering Contraceptive

In one embodiment, the specific alginic acid subsets described above can be part of an acid buffering contraceptive. One non-limiting example of such acid buffering contraceptive is Acidform (also known as Amphora® gel (U.S. Pat. No. 6,706,276, WO 01/66084)), which is a gel that, when placed in a body orifice (e.g., the vagina), forms a matrix upon contact with ejaculate and thus entraps and inactivates spermatozoa and/or STD and STI-causing microbes. In one general embodiment, the acid buffering contraceptive contains (1) a matrix-forming compound, (2) a bioadhesive compound, and (3) lactic acid. Some compounds, such as alginic acid, carrageenan, or chitosan, can act as both the matrix-forming compound and the bioadhesive compound.

In exemplary embodiments, the Acidform used generally contains (1) about 1-10% of one or more matrix-forming compounds, (2) about 1-10% of one or more bioadhesive compounds, and (3) about 1-10% of lactic acid. In other embodiments of, the Acidform composition contains (1) about 3-5% of one or more matrix-forming compounds, (2) about 2.5-6% of one or more bioadhesive compounds, and (3) about 1-7% of lactic acid. In other embodiments, the Acidform composition contains (1) about 3.5-4.5% of one or more matrix-forming compounds, (2) about 2.5-3.5% of one or more bioadhesive compounds, and (3) about 1-4% of lactic acid.

In other exemplary embodiment, the Acidform used generally contains (1) about 1-10% of one or more matrix-forming compounds, (2) about 1-10% of one or more bioadhesive compounds, and (3) about 1-10% of L-lactic acid. In other embodiments, the Acidform composition contains (1) about 3-5% of one or more matrix-forming compounds, (2) about 2.5-6% of one or more bioadhesive compounds, and (3) about 1-7% of L-lactic acid. In other embodiments, the Acidform composition contains (1) about 3.5-4.5% of one or more matrix-forming compounds, (2) about 2.5-3.5% of one or more bioadhesive compounds, and (3) about 1-4% of L-lactic acid.

Matrix-forming compounds suitable for use in the present disclosure should be stable over a wide pH range, especially over the normal acidic pH values found in the vagina. Suitable matrix-forming compounds include, for example, alginic acid, chitosan, gellan gum, poloxamer, carrageenan, iota carrageenan, and the like. The matrix-forming compound preferably stays in a non-matrix state until it comes in contact with ejaculate. Upon contact with ejaculate, the matrix-forming compound forms a semisolid matrix that traps sperm and STD-causing microbes so they cannot migrate through the lower female genital tract. Some matrix forming compounds, such as alginic acid, (which has a pH of about 1.5-3.5 in an aqueous solution), may contribute to the acid buffering capabilities of the acid buffering contraceptive. Furthermore, some matrix-forming compounds may also contribute to the bioadhesive nature of the acid buffering contraceptive. In some embodiments, the matrix-forming compound and bioadhesive compound are the same.

Bioadhesive compounds suitable for use in the present disclosure include, for example, xanthan gum, carrageenan, iota carrageenan, alginic acid, hydroxypropyl cellulose, hydroxypropyl methyl cellulose, sodium carboxymethyl cellulose, chitosan, polycarbophil, carbopol, and the like. In at least one embodiment, the bioadhesive compound is xanthan gum, a high molecular weight polysaccharide gum containing D-glucosyl, D-mannosyl, and D-glucosyluronic acid residues and varying proportions of O-acetyl and pyruvic acid acetal. The primary structure is a cellulose backbone with trisaccharide side chains; the repeating unit is a pentasaccharide. Generally, the molecular weight is greater than about 106 g/mole.

The acid buffering contraceptive further comprises lactic acid or other buffering agents that act to maintain the pH of the vagina within its normal acidic range (i.e., a pH of less than about 5 and more preferably in the range of about 3.5 to about 4.5) even in the presence of normal amounts of ejaculate. Besides lactic acid, suitable buffering agents include, but are not limited to, for example, citric acid, potassium acid tartrate, benzoic acid, alginic acid, sorbic acid, fumaric acid, ascorbic acid, stearic acid, oleic acid, tartaric acid, potassium bitartrate, benzoic acid, edetic acid ethylenediaminetetracetic acid, acetic acid, malic acid, and the like. The acids may be added as free acids, hydrates, or pharmaceutically acceptable salts. Of course, the free acids can be converted to the corresponding salts in situ (i.e., within the vagina). In various exemplary embodiments, several buffering agents are included in the Acidform composition to provide increased buffering capacity. Alginic acid, of course, can function as both a matrix-forming agent and a buffering agent. Since alginic acid will not be absorbed by the body, its acid buffering effect will be longer lasting as compared to the other buffering agents which may be absorbed by the body.

Accordingly, as discussed above, lactic acid or other suitable buffering agents may be used to maintain the pH of the vagina within its normal acidic range after application (i.e., a pH of less than about 5 and more preferably in the range of about 3.5 to about 4.5). In particular, it has been discovered that lactic acid significantly increases the microbicidal potency in relation to other natural vaginal defense mechanisms, such as hydrogen peroxide. This feature was previously unknown to those of skill in the art, and the inventors of the present disclosure have surprisingly found that the acid buffering contraceptive, when formulated using lactic acid as a buffering agent, possesses significantly greater microbicidal activity than formulations that do not use lactic acid as a buffering agent.

Specifically, the presence of lactic acid results in greater inactivation of microbes, including viruses, in comparison to compounds such as hydrogen peroxide or acetic acid at equivalent pH. The mechanism of action by which lactic acid increases microbicidal potency is believed to be the disruption of the cell membranes of gram-negative bacteria, and also acts to inactivate HIV and HSV-2.

More specifically, lactic acid has two isomers, one is known as L-(+)-lactic acid or (S)-lactic acid and the other is D-(−)-lactic acid or (R)-lactic acid. Recent discovery has shown that the L form of lactic acid is more potent in inactivating HIV than D or racemic lactic acid. While the precise mechanism of how L-lactic acid inactivates HIV is unknown, the stereochemical dependent activity suggests that it acts on proteins. (Purcell et al., AIDS Res Hum Retroviruses. 2012 Nov;28(11):1389-96.)

Lactic acid is produced by lactic acid bacteria such as *Lactobacillus* species. However, lactic acid bacteria generally produce both D and L lactic acid. Furthermore, lactic acid bacteria can be difficult to grow. Recombinant methods can be used to specifically manufacture L-lactic acid using hosts that easier to grow such as yeast or *Escherichia coli*. (Ishida et al., Appl Environ Microbiol. 2005 April; 71(4): 1964-1970 and Dien et al., J Ind Microbiol Biotechnol. 2001 Oct;27(4):259-64.) Alternatively, purified L-lactic acid can be purchased from established chemical suppliers such as Sigma-Aldrich® (St. Louis, Mo.).

In one embodiment the acid buffering contraceptive is further described as follows: the matrix-forming compound is alginic acid; the bioadhesive compound is xanthan gum, and/or hydroxycellulose, and/or carrageenan; lactic acid is used or is substituted by citric acid, benzoic acid or potassium acid tartrate; glycerol is included as a humectant; benzoic acid is used as a preservative; and water is the pharmaceutically acceptable carrier. In another embodiment, the composition contains xanthan gum, alginic acid, lactic acid, citric acid, benzoic acid, potassium bitartrate, glycerol, and water. In another embodiment, the lactic acid is L-lactic acid.

In another embodiment, the acid buffering contraceptive includes alginic acid, carrageenan, and lactic acid. In another embodiment, the acid buffering contraceptive includes alginic acid, carrageenan, lactic acid, citric acid, benzoid acid, potassium bitartrate, glycerol, and water. In another embodiment, the carrageenan is iota carrageenan. In another embodiment, the lactic acid is L-lactic acid.

Pharmaceutically Acceptable Carrier

In one embodiment, the pharmaceutical carrier is water. Other pharmaceutically acceptable carriers that are suitable for vaginal delivery are well known and can be used in place of water. One example of a suitable pharmaceutically acceptable carrier is petrolatum, such as white petrolatum.

Optional Ingredients

Additional optional excipients may be used in the compositions of the present disclosure such as buffering agents, thickeners, humectants, and preservatives. Suitable buffering agents include, but are not limited to, for example, lactic acid, citric acid, potassium acid tartrate, potassium bitartrate, benzoic acid, sorbic acid, fumaric acid, ascorbic acid, stearic acid, oleic acid, tartaric acid, edetic acid ethylenediaminetetracetic acid, acetic acid, malic acid, and the like. Suitable thickeners include, but are not limited to, for example, xanthan gum, hydroxypropyl cellulose, hydroxypropyl methyl cellulose, sodium carboxymethyl cellulose, chitosan, polycarbophil, carbopol, gellan gum, poloxamer, carrageenan, iota carrageenan, and the like. Suitable humectants include, but are not limited to, for example, glycerol, polyethylene glycols, propylene glycols, sorbitol, triacetin, and the like. In one exemplary embodiment, glycerol is used to prevent the formation of a dry film on the gel when placed within the vagina. Glycerol may also act as a lubricant. Additionally, the compositions may also include a preservative. Suitable preservatives include, but are not limited to, for example, benzoic acid, sodium benzoate, methylparaben, ethylparaben, butylparaben, propylparaben, benzyalkonium chloride, phenylmercuric nitrate, chlorhexidine, and the like. In one exemplary embodiment, benzoic acid is used and may also contribute to the buffering capacity of the Acidform gel.

Optional ingredients also include agents that enhance drug solubility, permeability and absorption. Non-limiting examples include pamoic acid (also called "embonic acid") and salts and esters thereof.

Formulation

The pharmaceutical composition may be in the form of a gel, a semi-solid, a cream, and/or a lotion. Generally, the alginic acid-based microbicide may be administered as a topical ointment applied to the lining of the vagina and/or cervix and/or rectum, which can be accomplished as a gel, cream, lotion, non-aqueous or aqueous solution used to flush the vaginal or rectal cavity, and/or a vaginal or rectal suppository. In other embodiments, the alginic acid-based microbicide composition may be administered in a spray formulation. In addition, the alginic acid-based microbicide compositions may be delivered using microbicide-impregnated diaphragms and female and male condoms.

Furthermore, in addition to the alginic acid-based microbicide compositions disclosed herein, the balance of the compositions, i.e., typically from about 0-10% weight, or from about 0.1-5% weight, or from about 0.1-3% weight, may optionally comprise one or more cosmetic ingredients. Such cosmetic ingredients are known to those skilled in the art and are often referred to in the art as diluents, solvents, and adjuvants. Typically, cosmetic ingredients include, for example; water, ethyl alcohol, isopropyl alcohol, glycerin, glycerol propylene glycol, sorbitol, and other high molecular weight alcohols. In addition, the compositions may contain minor amounts of other additives, such as, for example; stabilizers, surfactants, menthol, eucalyptus oil, other essential oils, fragrances, and the like. The selection and amounts of cosmetic ingredients, other additives, and blending procedures can be carried out in accordance with techniques well-known in the art.

Method of Manufacture

Tenofovir is an off-white powder with a molecular weight of 287.2 (anhydrous) or 305 (as monohydrate). It is not water soluble at an acidic pH and thus is not easily combinable with alginic acid. The present disclosure provides various manufacturing methods for combining tenofovir with alginic acid.

The final formulation should be viscous enough so that it remains in place without the use of physical devices. Compositions that are too thin will leak out and compositions that are too thick will be difficult to use properly, (e.g. smear to cover the vagina and cervix). Additionally, during use, dilution is expected to occur due to, for example, the presence of vaginal fluid and exposure to semen. The viscosity of the formulations described herein may be between 20,000-200,000 centipoise (cP) when the torque percentage is about 20%. Alternatively, the viscosity maybe between 30,000-150,000 cP.

The methods disclosed herein generally involve three steps. In the first step, tenofovir is dissolved in a basic solution. In the second step, the pH is brought to below neutral. In the third step, alginic acid is added. Optional ingredients, such as thickeners, humectants, or preservatives may be added during any of the steps so long as the optional ingredients do not affect the overall pH of the solutions in the various steps.

In one embodiment, the first step combines water, tenofovir, and sodium hydroxide. The second step adds lactic acid. The third step adds alginic acid. In another embodiment, the first step combines water, tenofovir, and sodium hydroxide. The second step adds lactic acid. The third step adds alginic acid and iota carrageenan. In yet another embodiment, the first step combines water, tenofovir, and sodium hydroxide. The second step adds L-lactic acid. The third step adds alginic acid and iota carrageenan.

The above-described method can also be used for incorporating the alginic acid-based microbicide into an acid buffering contraceptive. In one embodiment, the first step combines water, tenofovir, and sodium hydroxide. The second step adds lactic acid. The third step adds alginic acid and xanthan gum. Alternatively, the first step combines water, tenofovir, and sodium hydroxide. The second step adds citric acid and lactic acid. The third step adds alginic acid and xanthan gum. In another alternate method, the first step combines water, tenofovir, and sodium hydroxide. The second step adds benzoic acid, citric acid, and lactic acid. The third step adds alginic acid and xanthan gum. In yet another alternate method, the first step combines water, tenofovir, and sodium hydroxide. The second step adds benzoic acid, citric acid, potassium bitartrate, and lactic acid. The third step adds alginic acid and xanthan gum. In yet another alternate method, the first step combines water, tenofovir, and sodium hydroxide. The second step adds benzoic acid, citric acid, potassium bitartrate, and lactic acid. The third step adds alginic acid, glycerin, and xanthan gum.

In another embodiment, the first step combines water, tenofovir sodium hydroxide, and benzoic acid. The second step adds lactic acid. The third step adds alginic acid and xanthan gum. Alternatively, the first step combines water, tenofovir sodium hydroxide, and benzoic acid. The second step adds citric acid and lactic acid. The third step adds alginic acid and xanthan gum. In another alternate method, the first step combines water, tenofovir sodium hydroxide, and benzoic acid. The second step adds potassium bitartrate, citric acid, and lactic acid. The third step adds alginic acid and xanthan gum. In yet another alternate method, the first step combines water, tenofovir sodium hydroxide, and benzoic acid. The second step adds potassium bitartrate, citric acid, and lactic acid. The third step adds alginic acid, glycerin, and xanthan gum.

In yet another embodiment, the first step combines water, tenofovir, sodium hydroxide, benzoic acid, and potassium bitartrate. The second step adds lactic acid. The third step adds alginic acid and xanthan gum. Alternatively, the first step combines water, tenofovir, sodium hydroxide, benzoic acid, and potassium bitartrate. The second step adds citric acid and lactic acid. The third step adds alginic acid and xanthan gum. In another alternate method, the first step combines water, tenofovir, sodium hydroxide, benzoic acid, and potassium bitartrate. The second step adds citric acid and lactic acid. The third step adds alginic acid, glycerin, and xanthan gum.

In yet another embodiment, the first step combines water, tenofovir, and sodium hydroxide. The second step adds lactic acid. The third step adds alginic acid and iota carrageenan. Alternatively, the first step combines water, tenofovir, and sodium hydroxide. The second step adds citric acid and lactic acid. The third step adds alginic acid and iota carrageenan. In another alternate method, the first step combines water, tenofovir, and sodium hydroxide. The second step adds benzoic acid, citric acid, and lactic acid. The third step adds alginic acid and iota carrageenan. In yet another alternate method, the first step combines water, tenofovir, and sodium hydroxide. The second step adds benzoic acid, citric acid, potassium bitartrate, and lactic acid. The third step adds alginic acid and iota carrageenan. In yet another alternate method, the first step combines water, tenofovir, and sodium hydroxide. The second step adds benzoic acid, citric acid, potassium bitartrate, and lactic acid. The third step adds alginic acid, glycerin, and iota carrageenan.

In yet another embodiment, the first step combines water, tenofovir sodium hydroxide, and benzoic acid. The second step adds lactic acid. The third step adds alginic acid and iota carrageenan. Alternatively, the first step combines water, tenofovir sodium hydroxide, and benzoic acid. The second step adds citric acid and lactic acid. The third step adds alginic acid and iota carrageenan. In another alternate method, the first step combines water, tenofovir sodium hydroxide, and benzoic acid. The second step adds potassium bitartrate, citric acid, and lactic acid. The third step adds alginic acid and iota carrageenan. In yet another alternate method, the first step combines water, tenofovir sodium hydroxide, and benzoic acid. The second step adds potassium bitartrate, citric acid, and lactic acid. The third step adds alginic acid, glycerin, and iota carrageenan.

In yet another embodiment, the first step combines water, tenofovir, sodium hydroxide, benzoic acid, and potassium bitartrate. The second step adds lactic acid. The third step adds alginic acid and iota carrageenan. Alternatively, the first step combines water, tenofovir, sodium hydroxide, benzoic acid, and potassium bitartrate. The second step adds citric acid and lactic acid. The third step adds alginic acid and iota carrageenan. In another alternate method, the first step combines water, tenofovir, sodium hydroxide, benzoic acid, and potassium bitartrate. The second step adds citric acid and lactic acid. The third step adds alginic acid, glycerin, and iota carrageenan.

Methods of Use

In exemplary embodiments, the present disclosure involves the topical application of alginic acid-based antimicrobial compositions as described herein. In the context of the present disclosure, it is to be understood that the term "topical application" includes application to the body cavities as well as to the skin. Thus, for example, the aforementioned compositions are applied to a body cavity such as the vagina, anus, rectum or mouth. Furthermore, the topical application may be carried out before, during or after intercourse, or alternatively, carried out independent from intercourse.

It is to be understood that the alginic acid-based antimicrobial compositions of the present disclosure may be delivered to the vagina of a mammal by any means known to those skilled in the art. Typical forms for delivery of the compositions include, for example; creams, lotions, gels, foams, intervaginal devices such as sponges and suppositories, and films. In addition, the alginic acid-based antimicrobial compositions may be used as personal care products, such as, for example, condom lubricants, and the like. Such lubricants may comprise commonly known ingredients such as, for example: humectants, e.g., glycerin, sorbitol, mannitol, glycols and glycol ethers; buffers, e.g., glucono-d-lactone; germicides or bactericides, e.g., chlorhexidine gluconate; preservatives, e.g., methylparaben; viscosifiers, e.g., hydroxyethyl cellulose, etc.; other adjuvants, e.g., colors and fragrances; in addition to the compositions of the present disclosure. Those skilled in the art will recognize that the physical properties, e.g., viscosity, of such delivery forms may vary widely. For example, the viscosity of a gel form of the composition of the present disclosure, e.g. 150,000 centipoise, may be substantially higher than the viscosity of lotion form of the composition of the present disclosure, e.g., 100 centipoise. Further details concerning the materials, ingredients, proportions and procedures of such delivery forms can be selected in accordance with techniques well-known in the art.

In various embodiments, the alginic acid-based antimicrobial compositions of the present disclosure are preferably administered to the vagina of the mammal in a dosage which is effective to reduce the risk of STD transmission. Typical dosages range between about 1-10 grams, or between 3-7 grams, or between 4-6 grams of the composition. In various embodiments, the alginic acid-based antimicrobial compositions disclosed can be applied using a device or applicator such as a suppository, a sponge, a swab, a brush, or a syringe. In other embodiments, the alginic acid-based antimicrobial compositions disclosed can be applied to a barrier device such as a sponge, a condom or a diaphragm. In one embodiment, the alginic acid-based antimicrobial compositions disclosed can be in pre-filled single use devices such as a pre-filled squeezable tube or pre-filled syringe.

It will be readily apparent to those skilled in the art that other compounds functioning as precursors, analogs and derivatives such as salts and esters of the present compounds can be utilized.

The disclosure set forth above is provided to give those of ordinary skill in the art a complete disclosure and description of how to make and use embodiments of the compositions and methods, and are not intended to limit the scope of what the inventors regard as their invention. Modifications of the above-described modes (for carrying out the disclosure that are obvious to persons of skill in the art) are intended to be within the scope of the following claims. All publications, patents, and patent applications cited in this specification are incorporated herein by reference in their entirety as if each such publication, patent or patent application were specifically and individually indicated to be incorporated herein by reference.

EXAMPLES

The following formulations use a subset of alginic acid that has a molecular weight between 20,000 and 400,000 and an M:G ration between 0.25 and 2.0.

Example 1

Formulations for Alginic Acid-Based Microbicide

In its simplest form, the alginic acid-based microbicide contains alginic acid, tenofovir, and water. In another form, alginic acid, iota carrageenan, tenofovir, and water are combined. For any of the formulations mentioned herein, pamoic acid is optionally added to enhance the solubility, permeability, or absorption of tenofovir.

The formulations are made by dissolving tenofovir in a basic solution of water and sodium hydroxide. The pH is brought to below neutral and the alginic acid is added. Iota carrageenan, if being used, is added before, at the same time, or after the alginic acid.

Example 2

Formulations for Alginic Acid-Based Microbicide and Contraceptive

In its simplest form, the alginic acid-based microbicide and contraceptive contains alginic acid, tenofovir, lactic acid and water. In another form, alginic acid, xanthan gum, tenofovir, lactic acid, and water are combined. In another form, alginic acid, iota carrageenan, tenofovir, lactic acid, and water are combined. In another form, alginic acid, xanthan gum, tenofovir, lactic acid, citric acid, benzoic acid, potassium bitartrate, glycerin, and water are combined. In another form, alginic acid, iota carrageenan, tenofovir, lactic acid, citric acid, benzoic acid, potassium bitartrate, glycerin, and water are combined. For any of the formulations mentioned herein, pamoic acid is optionally added to enhance the solubility, permeability, or absorption of tenofovir.

The formulations are made by dissolving tenofovir in a basic solution of water and sodium hydroxide. The pH lowering ingredients, such as citric acid, lactic acid, and alginic acid are added next. Thickening agents, such as xanthan gum and iota carrageenan are added last. Other ingredients that do not affect the pH, such as glycerin, benzoic acid, and potassium bitartrate, can be added at any stage. The final pH should be similar to the normal vaginal pH range, such as between about 2 and about 5 or between about 2 and about 4, or between about 3 and about 4.

Example 3

Clinical Trials for an Acid Buffering Contraceptive, Amphora Gel

In this example, clinical trials were conducted to evaluate the contraceptive capabilities of an acid buffering contraceptive, Amphora gel. Amphora gel was compared to Conceptrol® vaginal gel (Revive Personal Products Company, Madison, N.J.) in a non-inferiority study. Conceptrol vaginal gel is a topical gel containing 4% nonoxynol-9 in a 2.5 mL volume of gel. Healthy women between the ages of 18-35 were enlisted in the clinical trial, half were given Amphora gel (5 mL dose per use) and the other half were given Conceptrol gel (2.5 mL dose per use). Women were instructed to vaginally insert the gel up to 2 hours before having heterosexual intercourse. Both gels were administered over a period of 7 menstrual cycles and a subset of users continued using Amphora gel for an additional 6 cycles. At the end of the evaluation period, a subset of women underwent colposcopy to detect lesions in the vaginal and cervix and testing to measure any changes in the vaginal flora.

The results indicated that Amphora gel was not inferior to Conceptrol vaginal gel for contraceptive purposes using Kaplan-Meier statistical analysis. Amphora gel was well tolerated and had no significant adverse event. The incidence of bacterial vaginosis, urinary tract infection, and yeast infections were similar between the two gels. Further, there were no reports of leakage of the Amphora gel and the women seemed to prefer Amphora gel.

The examples set forth above are provided to give those of ordinary skill in the art a complete disclosure and description of how to make and use embodiments of the compositions, and are not intended to limit the scope of what the inventors regard as their invention. Modifications of the above-described modes (for carrying out the invention that are obvious to persons of skill in the art) are intended to be within the scope of the following claims.

All references cited herein are hereby incorporated by reference.

What is claimed is:

1. A method of preventing conception comprising topically administering a contraceptive microbicide composition comprising about 3.5-4.5% alginic acid, about 2.5-3.5% of xanthan gum, and about 1-4% L-lactic acid, wherein the alginic acid has a ratio of mannuronate:guluronate residues between 0.3 and 1.5, wherein the composition is essentially free of D-lactic acid, wherein the topical administration comprises intravaginal administration.

2. The method of claim 1, wherein the contraceptive microbicide composition has a pH from about 1.5 to about 3.5.

3. The method of claim 1, wherein the contraceptive microbicide composition further comprises one or more of a buffering agent, a thickener, and a preservative.

4. The method of claim 3, wherein the buffering agent is selected from the group consisting of citric acid, potassium acid tartrate, benzoic acid, sorbic acid, fumaric acid, ascorbic acid, stearic acid, oleic acid, tartaric acid, potassium bitartrate, edetic acid ethylenediaminetetracetic acid, acetic acid, and malic acid.

5. The method of claim 3, wherein the thickener is selected from the group consisting of xanthan gum, hydroxypropyl cellulose, hydroxypropyl methyl cellulose, sodium carboxymethyl cellulose, chitosan, polycarbophil, gellan gum, poloxamer, carrageenan, iota carrageenan.

6. The method of claim 3, wherein the preservative is selected from the group consisting of benzoic acid, sodium benzoate, methylparaben, ethylparaben, butylparaben, propylparaben, benzyalkonium chloride, phenylmercuric nitrate, chlorhexidine.

7. The method of claim 1, wherein the contraceptive microbicide composition further comprises a pharmaceutically acceptable carrier.

8. The method of claim 7, wherein the pharmaceutically acceptable carrier is water or petrolatum.

9. The method of claim 1, wherein the contraceptive microbicide composition is topically applied prior to or after sexual activity.

10. The method of claim 9, wherein the contraceptive microbicide composition is applied at least 15 minutes or at least 30 minutes or at least 1 hour or at least 1.5 hours or at least 2 hours or at least 2.5 hours or at least 3 hours or at least 3.5 hours or at least 4 hours or at least 4.5 hours or at least 5 hours or at least 6 hour or at least 7 hours or at least 8 hours or at least 9 hours or at least 10 hours or at least or at least 12 hours prior to sexual activity.

11. The method of claim 9, wherein the contraceptive microbicide composition is applied within 5 minutes, or within 10 minutes, or within 15 minutes, or within 20 minutes, or within 30 minutes, or within 45 minutes, or within 1 hour, or within 2 hours, or within 3 hours, or within 4 hours, or within 5 hours, or within 6 hours, or within 7 hours, or within 8 hours, or within 9 hours, or within 10 hours after sexual activity.

12. The method of claim 1, wherein the contraceptive microbicide composition is administered at a dosage comprising about 1-10 grams, or about 3-7 grams, or about 4-6 grams of the composition.

13. The method of claim 1, wherein the alginic acid has a ratio of mannuronate:guluronate residues between 0.5 to 1.0.

14. The method of claim 13, wherein the ratio of mannuronate:guluronate residues is about 0.7.

15. The method of claim 1, wherein the alginic acid has a ratio of mannuronate:guluronate residues between 0.5 and 1.2.

16. The method of claim 1, the contraceptive microbicide composition further comprising citric acid, potassium bitartrate, glycerin, and benzoic acid.

17. A method of preventing conception comprising topically administering a contraceptive microbicide composition consisting essentially of about 3.5-4.5% alginic acid, about 2.5-3.5% of xanthan gum, about 1-4% L-lactic acid, citric acid, potassium bitartrate, glycerin, benzoic acid, and water, wherein the alginic acid has a ratio of mannuronate:guluronate residues between 0.3 and 1.5, wherein the topical administration comprises intravaginal administration, wherein the composition is essentially free of D-lactic acid.

18. The method of claim 17, wherein the contraceptive microbicide composition has a pH from about 1.5 to about 3.5.

19. The method of claim 17, wherein the alginic acid has a ratio of mannuronate:guluronate residues between 0.5 and 1.2.

* * * * *